United States Patent
Tanaka

(10) Patent No.: US 8,152,817 B2
(45) Date of Patent: Apr. 10, 2012

(54) INTRAOCULAR LENS INSERTION TOOL

(75) Inventor: Masayoshi Tanaka, Nagoya (JP)

(73) Assignee: Kowa Company Ltd., Nagoya (JP)

( * ) Notice: Subject to any disclaimer, the term of this patent is extended or adjusted under 35 U.S.C. 154(b) by 384 days.

(21) Appl. No.: 12/318,219

(22) Filed: Dec. 23, 2008

(65) Prior Publication Data

US 2009/0171365 A1    Jul. 2, 2009

(30) Foreign Application Priority Data

Dec. 28, 2007  (JP) .................................. 2007-341112

(51) Int. Cl.
*A61F 9/00*    (2006.01)

(52) U.S. Cl. ....................................................... 606/107

(58) Field of Classification Search .................. 606/107; 623/6.11, 6.12, 17.16; 604/15, 57, 59, 60; 221/240, 156–173

See application file for complete search history.

(56) References Cited

U.S. PATENT DOCUMENTS

| 2005/0222579 A1 * | 10/2005 | Vaquero et al. ............... 606/107 |
| 2006/0142780 A1 | 6/2006 | Pynson et al. |

FOREIGN PATENT DOCUMENTS

| EP | 1 857 074 A1 | 11/2007 |
| EP | 2 072 025 A1 | 6/2009 |
| JP | B-3412103 | 6/2003 |
| JP | B-3420724 | 6/2003 |
| WO | WO 98/12969 A1 | 4/1998 |
| WO | WO 2008/029498 A1 | 3/2008 |

OTHER PUBLICATIONS

Aug. 5, 2011 Office Action in Chinese Patent Application No. 200810185026.2 (with English translation).

* cited by examiner

*Primary Examiner* — Amy Lang

(74) *Attorney, Agent, or Firm* — Oliff & Berridge, PLC

(57) ABSTRACT

An intraocular lens insertion tool with a tool body for accommodating an intraocular lens and adapted to insert into an eye the intraocular lens through displacement of the lens in an axial forward direction by a plunging member, and to push out the lens through an insertion tube section disposed at an axial distal end of the tool body. A base plate of a resting portion that houses the lens is provided with side plates that respectively project from two widthwise edges of the base plate to both sides in a thickness direction of the base plate thereby imparting to the resting portion a generally "H" shaped cross section. The tool body inclusive of the resting portion and the insertion tube section is integrally formed from light-transmissive synthetic resin material whereby the lens housed within the resting portion is viewable from an outside through the base plate.

6 Claims, 12 Drawing Sheets

INTRAOCULAR LENS INSERTION TOOL

INCORPORATED BY REFERENCE

The disclosure of Japanese Patent Application No. 2007-341112 filed on Dec. 28, 2007 including the specification, drawings and abstract is incorporated herein by reference in its entirety.

BACKGROUND OF THE INVENTION

1. Field of the Invention

The present invention relates to an intraocular lens insertion tool used to insert an intraocular lens into the eye.

2. Description of the Related Art

One method employed in the past in the field of cataract surgery involves extracting the intracapsular crystalline lens through a surgical incision made in ocular tissue such as the cornea (sclera) or anterior capsule section of the crystalline lens, and once the crystalline lens has been removed, inserting an intraocular lens serving as a replacement for the crystalline lens back through the incision and positioning it within the capsule.

Particularly in recent years, methods that employ an intraocular lens insertion tool like that disclosed in Japanese Patent No. 3412103 or Japanese Patent No. 3420724 have come into widespread use. Typically, the intraocular lens will be inserted into the eye by first inserting the distal orifice of an insertion tube provided at the distal end section of the body of the tool through a surgical incision, then pushing the intraocular lens (which has been maintained in a state of compact deformation inside the body of the tool) out through the distal orifice of the insertion tube. By employing such an insertion tool, the intraocular lens can be inserted into the eye without expanding the surgical incision that was made for the purpose of extracting the crystalline lens, thereby reducing the labor entailed in the surgical operation, as well as reducing the risk of post-surgical astigmatism or infection.

Such a surgical operation to insert an intraocular lens into the eye of the patient requires reliability and rapidity. Therefore, a burden on the patient will be reduced and a risk of infection will be restrained.

In light of this objective, one important procedure during surgery is to visually check that the intraocular lens has been set at the prescribed location within the intraocular lens insertion tool being used, just prior to the surgical operation to insert the intraocular lens into the eye of the patient using the intraocular lens insertion tool. Additionally, in some cases it will be necessary to check that the intraocular lens that has been positioned in the intraocular lens insertion tool is not folded; or to check the position or shape of the haptics of the intraocular lens. Such visual inspection will be necessary both in cases where the intraocular lens is provided in a separate package from the intraocular lens insertion tool, and the intraocular lens must be positioned in the insertion tool prior to surgery; and in cases where the intraocular lens insertion tool is provided with intraocular lens already accommodated inside.

In order to make such visual inspection it would be conceivable to provide a recloseable cover at the site where the intraocular lens is positioned within the tool body of the intraocular lens insertion tool, and to perform visual inspection by opening and reclosing the cover. However, this requires a very tedious operation to open and reclose the cover, and is impractical due to the considerable wasted time and effort. Moreover, there is a risk that during the cover opening and reclosing operation, the tool body of the intraocular lens insertion tool will be subjected to shock, causing problems such as deformation or displacement of the intraocular lens that is housed inside.

Accordingly, it has been contemplated to fabricate the intraocular lens setting location of the tool body of the intraocular lens insertion tool of light-transmissive synthetic resin or similar material, so as to permit a visual examination of the intraocular lens to be made through the peripheral wall of the tool body once positioned inside.

However, since the intraocular lens itself is also transmissive of visible light, it will be necessary to make the peripheral wall of the tool body sufficiently thin so that the intraocular lens inside will be visible through the peripheral wall of the tool body. Thus, an associated problem is the difficulty of ensuring the component strength required of the tool body.

In order to address this problem, one conceivable approach would be for the tool body of the intraocular lens insertion tool to have as separate structures a section adapted to house the intraocular lens positioned therein, and a nozzle section situated at the distal end side thereof and adapted to guide the intraocular lens into the eye. By making the nozzle section a separate structure, it will be possible for the nozzle section only to be imparted with high strength; and by assembling this section together with the intraocular lens housing section, for the thin housing section to be reinforced by the nozzle section.

However, it is undesirable for the tool body to have such an assembled structure of several parts, not only due to the complexity of manufacture entailed by the increased number of parts but also to the risk that the intraocular lens insertion tool will be defective due to improper assembly.

SUMMARY OF THE INVENTION

It is therefore one object of this invention to provide an intraocular lens insertion tool of novel design having simple construction making it easy to manufacture, and whereby it will be possible to visually check from the outside the intraocular lens set therein during surgery, while maintaining sufficient strength on the part of the tool body.

The modes of the present invention addressed to solving the aforementioned objects will be discussed below. The constituent elements employed in each mode may be employed in any possible combination.

A first mode of the present invention provides an intraocular lens insertion tool comprising a tool body of generally tubular shape for accommodating an intraocular lens positioned therein, and including an insertion tube section disposed at an distal end section of the tool body in an axial direction; and a plunging member inserted into the tool body from a rear in the axial direction and moved forward for inserting into an eye the intraocular lens such that the intraocular lens undergoes compact deformation in association with forward displacement in the axial direction by the plunging member and is pushed out through the insertion tube section, wherein a resting portion that communicates with a basal end part of the insertion tube section is disposed in the tool body, a resting face adapted for resting the intraocular lens on a base plate of flat shape is formed in the resting portion, and side plates that respectively project to both sides in a thickness direction of the base plate are formed at two widthwise edges of the base plate thereby imparting to the resting portion a generally "H" shaped cross section; and the tool body inclusive of the resting portion and the insertion tube section is integrally formed from light-transmissive synthetic resin material whereby the intraocular lens positioned resting on the resting face of the resting portion is viewable from an outside through the base plate.

In the intraocular lens insertion tool constructed according to the present mode, in the resting portion of the tool body adapted to receive the intraocular lens the two widthwise edges of the base plate will ensure a large cross sectional area, owing to the pair of side plates. Consequently, in the event that the base plate is subjected to external force or moment in any of various directions, including the direction perpendicular to the plane in particular, it will be possible to establish large cross-sectional secondary moment due to the pair of side plates that jut up to locations away from the base plate at either side thereof in the thickness direction. Thus, a high level of bending rigidity can be efficiently ensured, despite the thinness of the base plate.

For this reason, it will be possible to realize a tool body that, while ensuring sufficient strength, is provided as a single molded component with a thin base plate. Through this base plate it will be possible inter alia to easily carry out visual inspection from the outside of the intraocular lens that has been positioned housed inside the resting portion.

A second mode of the present invention provides an intraocular lens insertion tool according to the first mode wherein through-holes are formed in the base plate; a support member is attached to the base plate from the outside, and support portions that project out from the support member are passed through the through-holes so as to project out on the resting face; an outside peripheral section of the lens rests on the support portions to support intraocular lens in the resting portion with a prescribed gap between the resting face and a center section of the intraocular lens; and support of the intraocular lens by the support portion is released by outwardly displacing the support member with respect to the base plate to extract the support parts which projected out on the resting face and position the intraocular lens resting on the resting face.

The intraocular lens insertion tool constructed according to the present mode can be provided in a form with the intraocular lens housed in the resting portion while supported on the support portions. For this reason, no laborious procedure to position the intraocular lens in the insertion tool will be required on-site during the surgical operation, thus making the surgical procedure simpler and faster. During this time, the intraocular lens will be supported in an uplifted condition above the resting face by being supported at its outside peripheral edge by the support portions, and just prior to surgery the intraocular lens will be positioned resting directly on the resting face by extracting the support portions. It will thus be possible to effectively avoid problems such as warping or damage to the optically crucial lens center section of the intraocular lens due to prolonged contact against the resting face.

In the present mode, it is sufficient for the intraocular lens housed in the resting portion to be visible through the base plate, at least when the support member has been detached from the tool body so that the base plate of the tool body is viewable directly.

In the present mode, in order to prevent the support member from unexpectedly detaching from the tool body, it will be preferable to employ a releasable catch mechanism (locking mechanism) for positioning the support member with respect to the tool body, with the support portions passed through the through-holes and projecting out on the resting face. No particular limitation is imposed on the specific structure of the locking mechanism; for example, the locking mechanism could be constituted by providing mating parts that mate with one another at appropriate locations on the support member and the tool body respectively; or the locking mechanism could be constituted by giving the support portions gradually larger contours with progressively greater projecting distance out from the through-holes of the resting face, with the support member being fastened to the outside of the resting face by pushing the support portions into the through-holes.

A third mode of the present invention provides an intraocular lens insertion tool according to the first or second mode wherein the resting portion is provided with an opening that opens to the outside of the tool body, and with a cover body adapted to cover the opening.

In the intraocular lens insertion tool constructed according to the present mode, shifting out of position or deformation of the intraocular lens housed therein can be corrected easily through the recloseable opening. Also, the mating action of the cover body with the opening can be utilized for additional reinforcing effect of the resting portion.

A fourth mode of the present invention provides an intraocular lens insertion tool according to any of the first to third modes wherein the support member is provided with a mating projection that with the support member attached from an outside to the base plate is adapted to slip between opposing faces of pair of side plates that have been formed at the two widthwise edges of the base plate; and the mating projection is provided at an outside end part thereof with leg plate parts disposed at outside the side plates and respectively extending beyond the side plates and flaring to either side in a width direction of the base plate.

In the intraocular lens insertion tool constructed according to the present mode, the pair of side plates that have been formed on the tool body can be utilized to realize a guide mechanism when attaching or detaching the support member. For this reason, it will be possible to carry out the operation to attach or detach the support member to or form the tool body with a greater level of ease.

By attaching the mating projection of the support member in a condition of abutment against or proximity to the pair of side plates of the tool body, there will also be provided a reinforcing effect whereby deformation-induced contact of the side walls of the tool body against the mating projection of the support member will inhibit further deformation.

Further, by providing leg plate parts that project out to either side in the width direction from the tool body at the outside of the base plate part, the strength of the support member, and hence the strength of the tool body (which is reinforced by the tool body), can be enhanced further; and since by utilizing the leg plate parts it is possible for the support member to be grasped easily with the hand, it will be possible for the operation to be carried out more easily when attaching or detaching the support member to or from the tool body.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
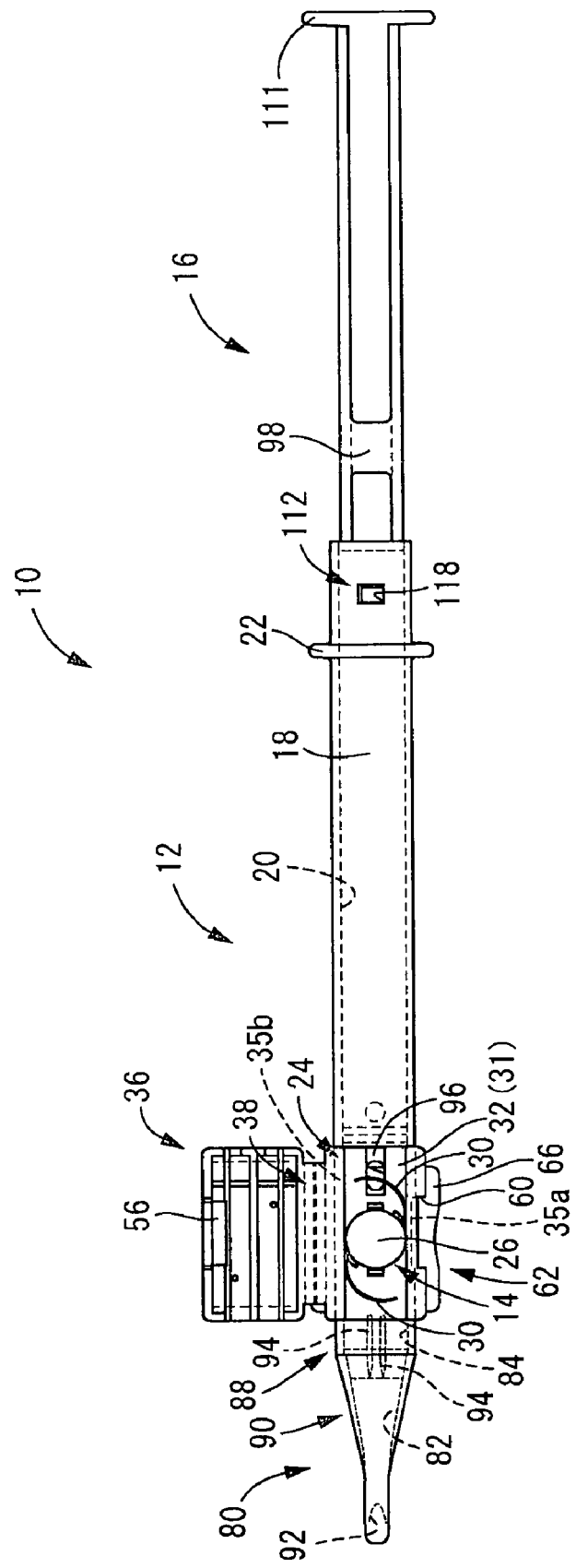
FIG. 1 is a top plane view of an intraocular lens insertion tool according to a first embodiment of the present invention.
Figure 2:
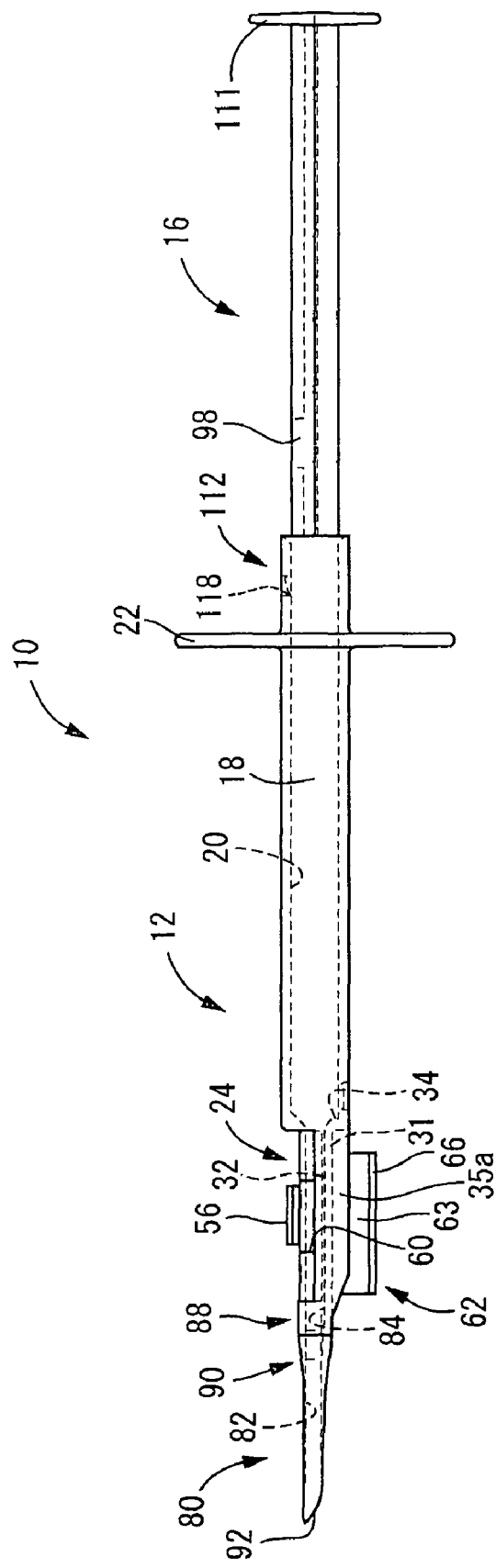
FIG. 2 is a side elevational view of the intraocular lens insertion tool of FIG. 1.
Figure 3:
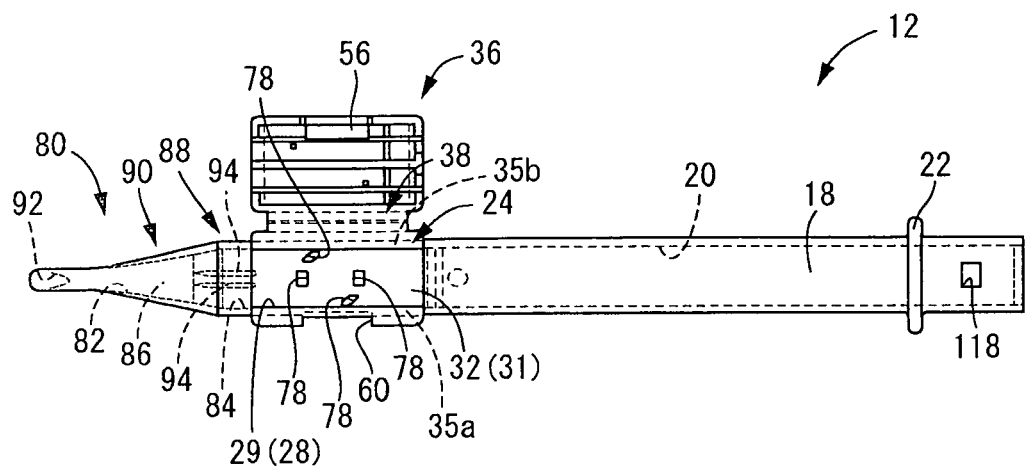
FIG. 3 is a top plane view of a tool body of the intraocular lens insertion tool of FIG. 1.
Figure 4:
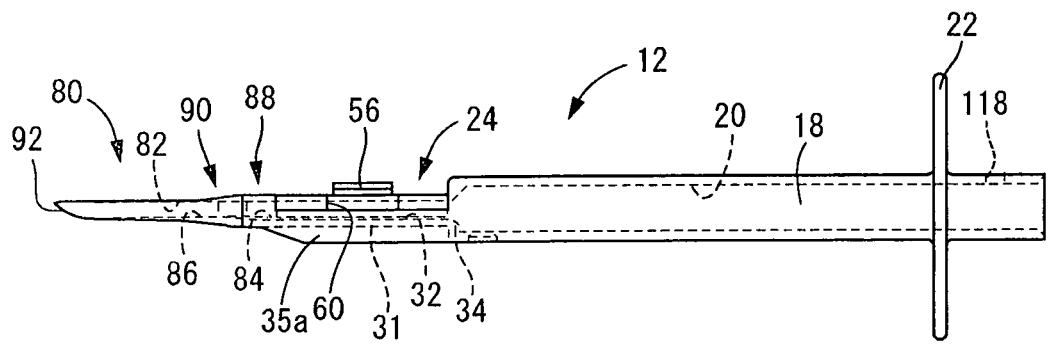
FIG. 4 is a side elevational view of the tool body of FIG. 3.
Figure 5:
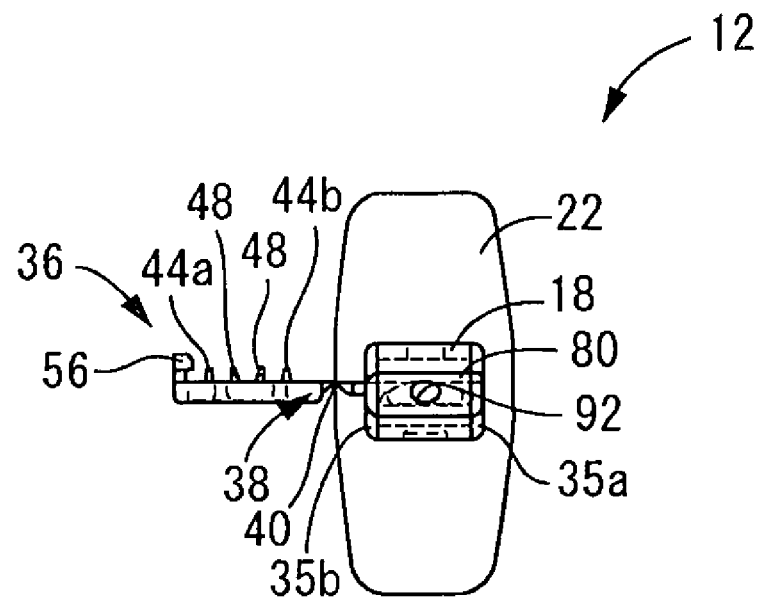
FIG. 5 is a front elevational view of the tool body of FIG. 3.
Figure 6:
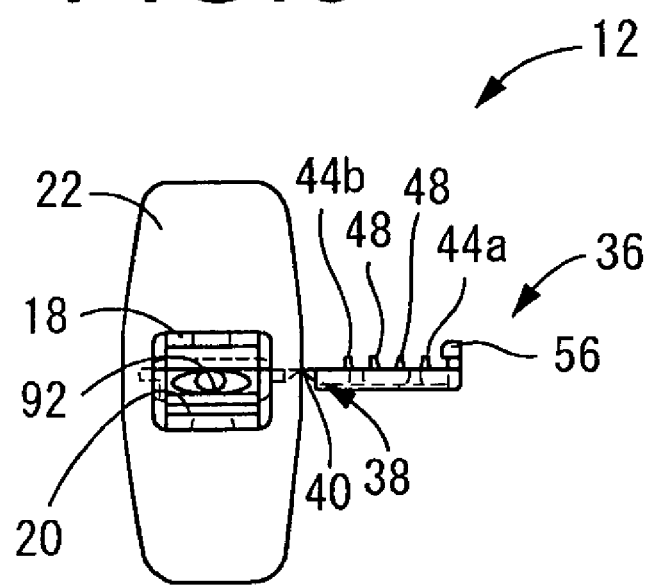
FIG. 6 is a rear elevational view of the tool body of FIG. 3.

First, an intraocular lens insertion tool 10 according to a first embodiment of the present invention is depicted in FIGS. 1 and 2. The insertion tool 10 is adapted to accommodate an intraocular lens 14 in the interior of a tool body 12 having generally tubular shape perforated in its interior throughout its entire length and open at the front and back ends, into which inserts a plunger 16 serving as a plunger member. Herein, 'front' refers to the plunging direction of the plunger 16 (leftward in FIG. 1), and 'upward' refers to the upward direction in FIG. 2. 'Left-right direction' refers to the left-right direction of the insertion tool 10 in rear view (in FIG. 1, the upward direction is right and the downward direction is left).

To describe in greater detail, as depicted in FIGS. 3 to 6, the tool body 12 has a main tubular section 18 of generally tubular shape. A through-bore 20 is formed in the interior of the main tubular section 18 and with generally oblong cross section passes therethrough in the axial direction. A plate-like portion 22 that extends on the perpendicular to the direction of extension of the main tubular section 18 is integrally formed at a location somewhat to the front of the back end of the main tubular section 18.

Figure 7:
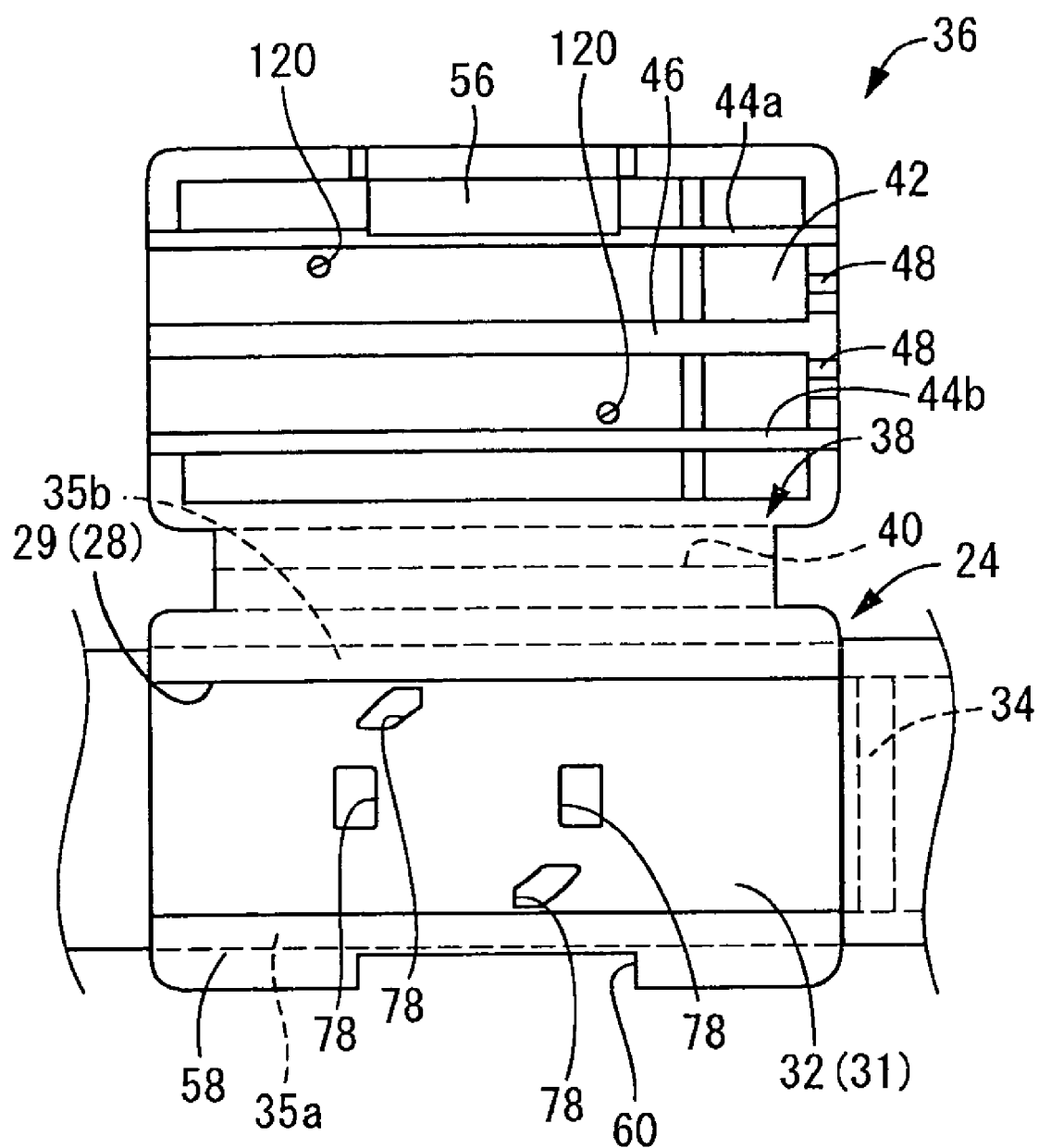
FIG. 7 is a fragmentary enlarged top plane view of the tool body of FIG. 3.

A stage 24 is provided as a resting portion at the front of the main tubular section 18 in the tool body 12. FIG. 7 depicts the stage 24. In the stage 24 there is formed a recessed slot 28 of width dimension slightly larger than the diameter dimension of the main body 26 of the intraocular lens 14 and extending in the axial direction. The recessed slot 28 has lengthwise dimension in the axial direction that is somewhat larger than the maximum width dimension (dimension in the left-right direction in FIG. 1) of the intraocular lens 14 inclusive of haptics 30, 30 that extend to either side thereof.

Here, the recessed slot 28 is of slot shape having an opening 29 that opens upward; its base face constitutes a resting face 32 that is defined by the upper face of the base plate 31. The base plate 31 has a thin, flat plate shape whose thickness dimension will be 3 mm or less, more preferably 1 mm or less, in order to effectively afford the desired visibility effect, described later. A zone on the upper face of the base plate 31 overlapping in the vertical direction the opening 29 constitutes the resting face 32. In preferred practice, with regard to the base plate 31, a thick part whose surface is continuous with that of the resting face 32 will be formed to a least one of the front and back sides in the plunging direction of the intraocular lens 14, in other words the axial direction of the tool body 12. In the present embodiment, the axial back edge part of the base plate 31 connects with the upper edge part of a wall part 34 that extends upward from the base face of the through-bore 20 at the front edge part of the through-bore 20 in the main tubular section 18, with the surfaces of the resting face 32 and the wall part 34 being continuous. By so doing, a thick part constituted by the wall part 34 will be provided at the axial back edge of the base plate 31. The height location of the resting face 32 defined by the upper face of the base plate 31 will be positioned above the base face of the through-bore 20.

Additionally, the base plate 31 has a width dimension slightly larger than the minimum width dimension (the vertical dimension in FIG. 1) of the intraocular lens 14; and is formed with an axial length dimension that is greater than the maximum width dimension (the left-right dimension in FIG. 1) of the intraocular lens 14. It is possible thereby for the intraocular lens 14 to rest without deformation on the resting face 32 that is constituted by the upper face of the base plate 31. The zone that constitutes the resting face 32 on the base plate 31 is a flat surface devoid of contours on both its front and back sides.

Additionally, at the two widthwise edges of the base plate 31 there are integrally formed side plates 35a, 35b having a thickness dimension greater than the thickness dimension of the base plate 31 and that project out to both sides in the thickness direction of the base plate 31. In preferred practice the side plates 35a, 35b will be formed so as to extend continuously with the resting face 32 towards at least the forward or rearward direction in the plunging direction of the intraocular lens 14, in other words the axial direction of the tool body 12; and more preferably will have a structure extending continuously across the entire length of the tool body 12 with the exception of a nozzle part 80, discussed later. In the present embodiment, the side plates 35a, 35b have been integrally formed with the main tubular section 18 by extending the two widthwise wall parts of the main tubular section 18 forward in the axial direction of the tool body 12 with generally unchanging height dimension; and by being made continuous with the two widthwise wall parts of the main tubular section 18, have been formed so as to extend in the axial direction of the tool body 12 along approximately the entirety of the tool body 12 with the exception of the nozzle part 80. In the present embodiment, the side plates 35a, 35b have gradually decreasing height dimension going from the front end of the resting face 32 to the back end part of the nozzle part 80, discussed later.

The base plate 31 and the upwardly projection sections of the resting face 32 at the side plates 35a, 35b define the recessed slot 28 of slot shape open at the top; and owing to the continuous surfaces of the resting face 32 and the wall part 34, a stage 24 whose design includes the recessed slot 28 will communicate with the through-bore 20. The stage 24 in axial sectional view will have a generally "H" shape, due to the side plates 35a, 35b projecting both up and down at the two widthwise edges of the base plate 31 (see FIG. 15).

To one side of the recessed slot 28 (in the present embodiment, the right side), a cover part 36 provided as the cover body is integrally formed with the tool body 12. The axial dimension of the cover part 36 is approximately equal to the axial dimension of the recessed slot 28, and its width dimension is somewhat larger than the width dimension of the recessed slot 28. Furthermore, the cover part 36 is connected to the tool body 12 by a linking part 38 of generally thin plate shape formed by extending the upper edge of the side plate 35b to the side (in the present embodiment, the right side). The linking part 38 is thinnest in a bending part 40 that extends through its approximately widthwise center section in the axial direction of the tool body 12, and is adapted to bend in this bending part 40. The cover part 36 can thereby be superposed over the recessed slot 28 by bending the linking part 38, so as to cover the opening 29.

On an opposed face 42 (the face positioned in opposition to the resting face 32) of the cover part 36 there are integrally formed a pair of left and right guide plate parts 44a, 44b provided by way of a pair of guide projections extending in the axial direction of the tool body 12. These left and right guide plate parts 44a, 44b are formed along the entire axial extension of the cover part 36, with the distance between their opposing faces being somewhat smaller than the width dimension of the recessed slot 28. The outside peripheral edge of the opposed face 42 is slightly thicker about the entire periphery, and the left and right guide plate parts 44a, 44b project out beyond the outside peripheral edge of the opposed face 42.

A center guide plate part 46 provided as a guide projection that extends parallel with the left and right guide plate parts 44a, 44b in the axial direction of the tool body 12 is integrally formed on the opposed face 42, at the approximate center location between the opposing faces of the left and right guide plate parts 44a, 44b. The center guide plate part 46 has a heightwise dimension that is equal to a heightwise dimension of the thick outside peripheral edge of the opposed face 42, and is integrally formed so as to extend from the outside peripheral edge along the entire length of the opposed face 42 in the axial direction. A pair of guide projections 48, 48 are formed to either side of the center guide plate part 46 in the zone of connection of the outside peripheral edge of the opposed face 42 with the axial rear edge of the center guide plate part 46. The guide projections 48 have generally triangular cross section and are integrally formed so as to project up from the outside peripheral edge of the opposed face 42, the projecting dimension thereof being approximately equal to the projecting dimension of the left and right guide plate parts 44a, 44b.

Additionally, a catch piece 56 is formed on the cover part 36 on the edge lying opposite from the linking part 38. A projecting edge part 58 projecting outwardly from the upper edge of the side plate 35a is formed on the stage 24 on the edge thereof lying opposite from the cover part 36; and a catch notch 60 is formed in the projecting edge part 58 at a location corresponding to this catch piece 56.

Figure 8:
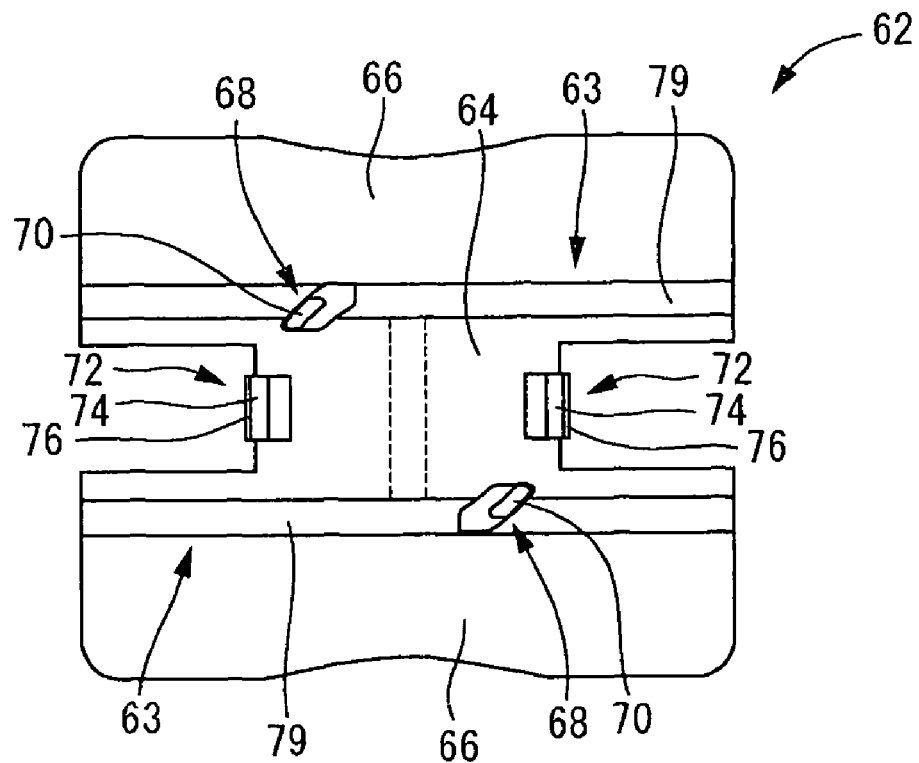
FIG. 8 is an top plane view of a support member of the intraocular lens insertion tool of FIG. 1.
Figure 9:
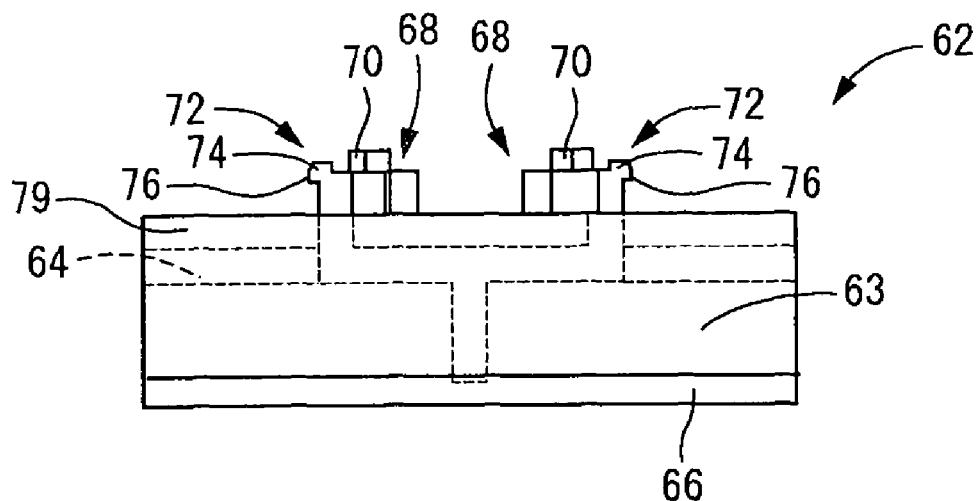
FIG. 9 is a side elevational view of the support member of FIG. 8.

A support member 62 is detachably disposed below the resting face 32 of the stage 24 having the above construction. As depicted in FIGS. 8 and 9, the support member 62 is constituted as a separate member from the tool body 12, and side wall parts 63, 63, which respectively project to both sides in the vertical direction, are integrally formed at the two widthwise edges of a linking plate part 64 of planer shape of a generally "H" shaped cross section in top view. Here, the distance separating the outside faces of the side wall parts 63 will be approximately equal to the diameter dimension of the main body 26 of the intraocular lens 14. A leg plate part 66 that projects out and flares outwardly is integrally formed on the lower edge of each of the side wall parts 63. The leg plate part 66 extends over an entire of each side wall part 63 in its front-back direction (left-right direction in FIG. 8), and has a slightly recessed contour in the center section in the axial direction in top view. At the central part of the linking plate part 64, a planer shape part is formed so as to extend in the widthwise direction while projecting downward, and the two widthwise edges of the planer shape part is held in connect with the inside faces of the side wall parts 63, 63.

At the upper edge part of each of the side wall parts 63, 63 there is integrally formed a first support part 68 provided as a support portion that projects upward in generally arcuate contour in top view. In the outside section of the upper end face of each first support part 68, a projecting peripheral wall 70 is integrally formed towards the inward side of the support member 62. Here, the distance separating the peripheral walls 70 will be slightly larger than the diameter dimension of the main body 26 of the intraocular lens 14.

A pair of second support parts 72, 72 provided as support portions that project upwardly with oblong shape in top view are integrally formed at both axial ends of the linking plate part 64. Here, the heightwise location of the upper end faces of the second support parts 72 are equivalent to the heightwise location of the upper end faces of the first support parts 68. Additionally, on the upper face of each second support part 72, towards the outside of the support member 62, there is integrally formed a peripheral wall 74 that projects upward along the entire width of the second support part 72; the distance separating the peripheral walls 74 will be slightly larger than the diameter dimension of the main body 26 of the intraocular lens 14. Also, a catch hook 76 that projects slightly outward is formed along the entire width of the second support part 72 at its upper edge.

The support member 62 having the above construction is adapted for attachment from below the base plate 31 of the tool body 12. Specifically, through-holes 78 formed in the base plate 31 of the tool body 12 pass through it in the thickness direction. The through-holes 78 have shape similar to but slightly larger than that of the first support parts 68 and the second support parts 72 in top view, and are formed at locations corresponding to the first support parts 68 and the second support parts 72 in top view. Preferably, at least one of the through-holes 78 is formed on the resting face 32, and all the through-holes 78 are formed on the resting face 32 in this embodiment.

The first support parts 68 and the second support parts 72 of the support member 62 will be passed through the through-holes 78 from the lower side of the resting face 32 so as to project above the resting face 32. By so doing, the catch hooks 76 provided to the second support parts 72 will project above the resting face 32 and become engaged with the upper face of the resting face 32, thereby preventing the first support parts 68 and the second support parts 72 from becoming detached, and holding the support member 62 in a state of attachment from the outside of the tool body 12 with the first support parts 68 and the second support parts 72 projecting above the resting face 32. In the present embodiment, the catch hooks 76 are included in the locking mechanism that locks the support member 62 to the tool body 12.

Figure 15:
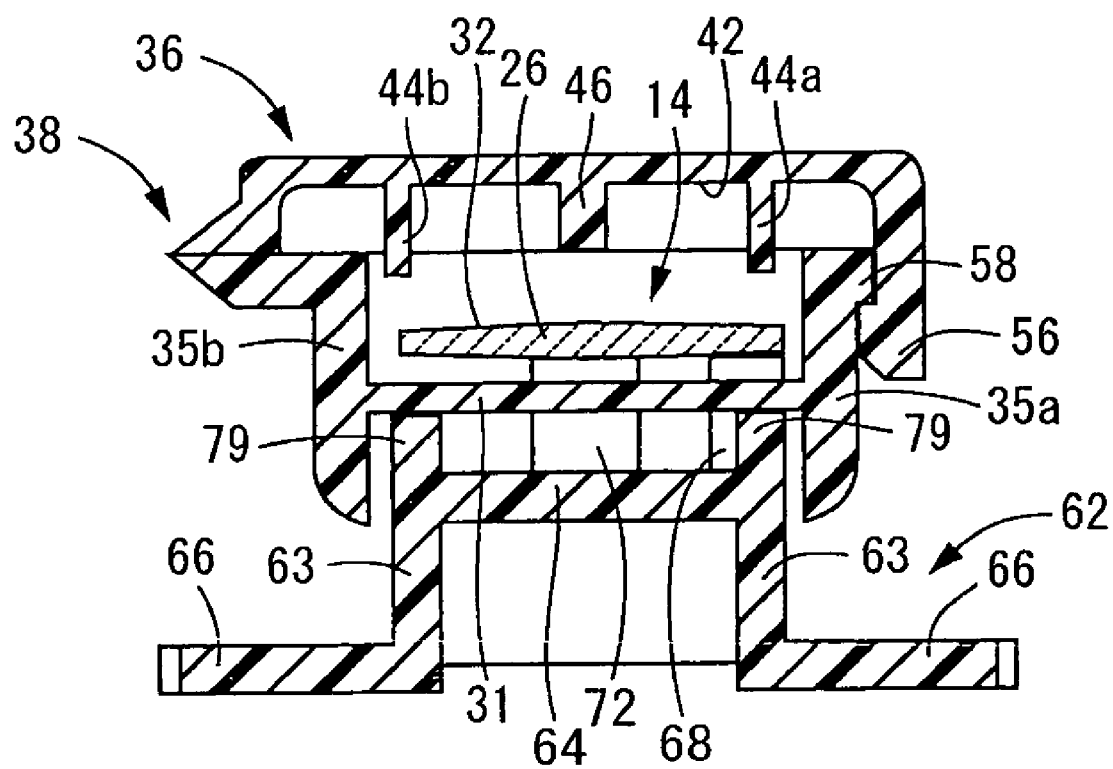
FIG. 15 is a cross sectional view taken along line 15-15 of FIG. 14A.

Here, the distance separating the outside faces of the side wall parts 63, 63 is made slightly smaller than the width dimension of the base plate 31 (see FIG. 15). Accordingly, with the support member 62 attached to the lower side of the base plate 31, the projecting sections of the side wall parts 63, 63 which project upward from the linking plate part 64 are adapted to slip between opposing faces of the side plates 35a, 35b so as to be inserted between the side plates 35a, 35b which project downward from the two widthwise edges of the base plate 31. As described, in the present embodiment, the projecting sections of the side wall parts 63, 63 which project upward from the linking plate part 64 are defined as a mating projection 79. In addition, with the support member 62 attached to the tool body 12, the leg plate parts 66, 66 project outward of the side plates 35a, 35b in top view so as to flare to either side in the width direction of the base plate 31.

Additionally, a nozzle part 80 provided as an insertion tube section is integrally formed at the axial distal end of the tool body 12, to the front of the stage 24. The nozzle part 80 as a whole has outside contours that gradually narrow from the basal end (towards the stage 24) towards the distal end in the direction of its extension, and has a bore 82 that passes through its entire length in the direction of its extension.

The bore 82 communicates with the stage 24 through connection of a basal end orifice 84 that opens towards the stage 24 to the resting face 32. The basal end orifice 84 as a whole has a flattened, generally elliptical cross section with a base face 86 defined by a flat face, and an upper face with a generally arcuate contour. Here, a guide part 88 formed by the base face 86 connecting steplessly to the resting face 32 is formed in the bore 82. The guide part 88 has a flattened, generally elliptical cross section, and extends in the axial direction of the tool body 12 with generally unchanging width dimension and height dimension from the basal end orifice 84.

Also formed in the bore 82 is a constricted-diameter part 90 that communicates with the guide part 88 to the front of the guide part 88, and that has gradually decreasing cross sectional area. The bore 82 has a shape extending straightly from the distal end of the constricted-diameter part 90 toward a distal end opening 92 with generally unchanging cross sectional area. The constricted-diameter part 90 decreases in cross sectional area towards its distal end owing to decreasing width dimension of the base face 86 and the upper face. The base face 86 of the back end section of the constricted-diameter part 90 is formed to incline gradually upward towards the front in the axial direction. The heightwise position of the upper face of the bore 82 is generally unchanging along its entire length in the axial direction. The distal end opening 92 has a diagonal orifice shape in side view whose upper face extends further forward than the lower face.

Additionally, a pair of guide projecting parts 94 that extend in the axial direction of the tool body 12 with the widthwise center section of the base face 86 between them is formed on the base face 86 of the guide part 88 and the constricted-diameter part 90. The guide projecting parts 94 have linear contours that project slightly up from the base face 86 and extend parallel to one another. The guide projecting parts 94 are made flat with the base face 86 at the rear end part of the constricted-diameter part 90, since the height of the base face 86 at the rear end part of the constricted-diameter part 90 gradually increases as it goes forwards in the axial direction of the tool body 12. As will be understood from the above description, the guide projecting parts 94 are formed at a position separate from the resting face 32, so that the resting face 32 is made flat over an entire area in the axial direction.

Furthermore, in preferred practice the guide projecting parts 94 will be arranged approximately parallel a prescribed distance apart from one another in the axis-perpendicular direction of the tool body 12 with the widthwise center of the base face 86 between them. The distance separating the guide projecting parts 94 will be slightly larger than the width dimension of the distal end part of the plunger member. In the present embodiment in particular, they are slightly larger than the width dimension of a rod-like part 100 of the plunger 16, described later.

As will be apparent from the above, the tool body 12 of the present embodiment is constituted as a single component integrally formed by the main tubular section 18, the stage 24, the cover part 36, and the nozzle part 80. The support member 62, which is constituted as a separate member from the tool body 12, is attached below the resting face 32. In preferred practice the tool body 12, inclusive of the nozzle part 80 and the base plate 31 that makes up the stage 24, will be integrally formed of synthetic resin material having high visible light transmissivity, such as a polyethylene or polypropylene for example; still more preferably, the support member 62 will be made of synthetic resin material having high visible light transmissivity like that of the tool body 12. Particularly with a view to improving visibility of the intraocular lens 14 from the outside at the front and back surfaces of the base plate 31, it will be preferable to employ a resin-forming mold in which the molding faces for molding these surfaces have been designed with high precision approximating a mirror finish.

By so doing, in the insertion tool 10 of the present embodiment, even with the opening 29 of the stage 24 covered by the cover part 36, it will be possible for at least the contours of the intraocular lens 14 housed within the tool body 12 to be visible to the eye from above the tool body 12 through the cover part 36. Additionally, it will be possible for at least the contours of the intraocular lens 14 housed within the tool body 12 to be visible to the eye from below the tool body 12, either through the support member 62 and base plate 31 if the support member 62 is attached, or through the base plate 31 if the support member 62 has been detached.

Figure 10:
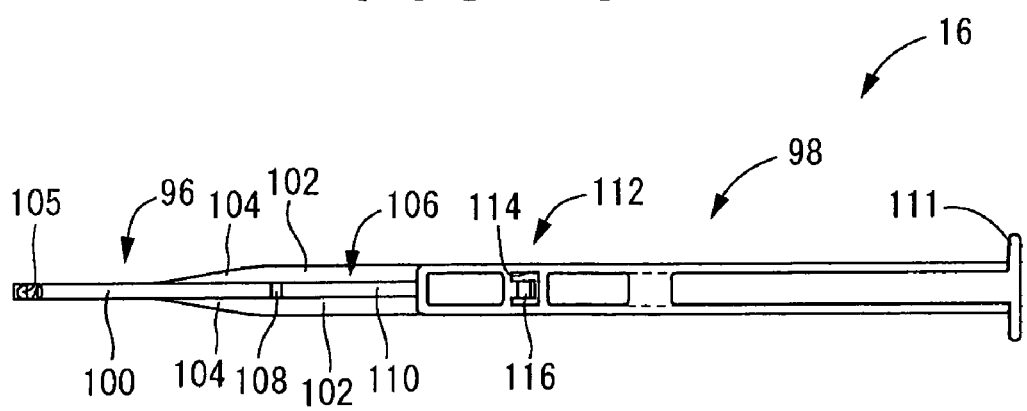
FIG. 10 is a top plane view of a plunger of the intraocular lens insertion tool of FIG. 1.
Figure 11:
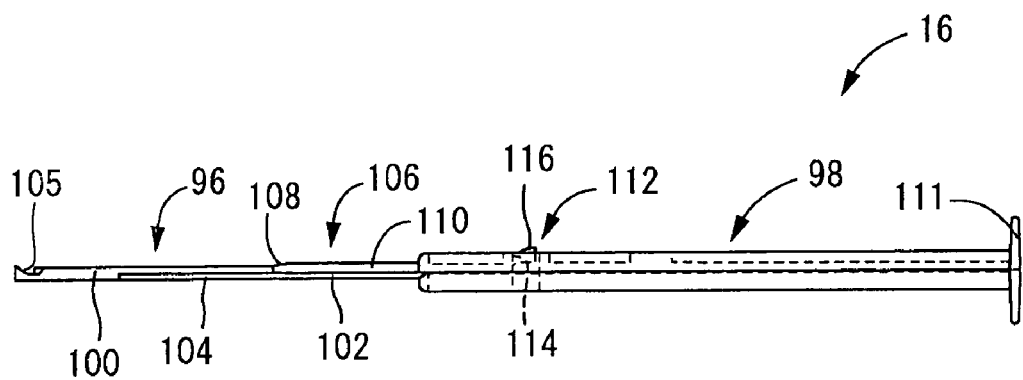
FIG. 11 is a side elevational view of the plunger of FIG. 10.

A plunger 16 provided as the plunger member is inserted into the through-bore 20 from the back of the tool body 12 having the above structure. The plunger 16 is depicted in FIGS. 10 and 11. The plunger 16 is of generally rod shape having axial length dimension somewhat larger than the axial length dimension of the tool body 12; and includes an integrally formed working part 96 of generally circular rod shape and a pass-through part 98 of generally oblong rod shape.

The working part 96 includes a rod-like part 100 of generally circular rod shape extending along the center axis of the plunger 16; and flattened parts 102 of thin plate form extending to either side in the width direction of the rod-like part 100. The flattened parts 102 extend from the back end of the rod-like part 100 towards the distal end direction with a width dimension equal to that of the pass-through part 98; and starting at the approximately medial section in the lengthwise direction of the rod-like part 100 have pointed parts 104 of gradually decreasing width dimension towards a zone somewhat rearward from the distal end part of the rod-like part 100. Here, the contours of the pointed parts 104 in top view conform in shape to the horizontal cross section of the constricted-diameter part 90 in the nozzle part 80 of the tool body 12.

Additionally, a notch 105 is formed in the axial distal end section of the working part 96. In the present embodiment, the notch 105 opens upward and to either side in the width direction; its inside peripheral face at the back end side in the axial direction in top view extends on the diagonal with respect to the axial direction of the working part 96 and spreads in the axis-perpendicular direction of the working part 96; while its inside peripheral face at the distal end side in the axial direction is defined as an inclined face that in top view extends in the axis-perpendicular direction of the working part 96 and heads upward toward the distal end of the working part 96.

Additionally, an upwardly projecting upward projecting portion 106 is formed somewhat to the rear of the axial medial section of the working part 96. The upward projecting portion 106 has a width dimension equal to the width dimension of the rod-like part 100; an inclined face 108 inclined upward going towards the rear is formed across prescribed dimensions at a location somewhat to rear from the axial medial section of the rod-like part 100, and a flat part 110 provided as a flat face whose upper end has unchanging height dimension is formed across from the back edge part of the inclined face 108 to the back edge part of the working part 96.

Meanwhile, the pass-through part 98 has an axial dimension that is slightly larger than the axial dimension of the through-bore 20. The pass-through part 98 in substantially the entirety thereof has a generally "H" shaped transverse section of width and height dimensions slightly smaller than the width and height dimensions of the through-bore 20. A pusher plate 111 of circular plate shape that extends in the axis-perpendicular direction is integrally formed at the back edge part of the pass-through part 98.

Additionally, a catch part 112 provided as retaining means is formed somewhat frontward from the axial medial section of the pass-through part 98. On the catch part 112 there is formed a hook part 116 that juts into a window part 114 perforating the pass-through part 98 in the axis-perpendicular direction, and that projects upward from the pass-through part 98. With the plunger 16 passed through the main tubular section 18 of the tool body 12, the hook part 116 of the plunger 16 will come into engagement with a catch hole 118 that perforates the upper face of the main tubular section 18 in the thickness direction, thereby holding the plunger 16 so that it is positioned relative to the tool body 12 while passing through it. The locations for forming the hook part 116 and the catch hole 118 are established such that, in the engaged state, the distal end part of the working part 96 will project out from the through-bore 20 of the tool body 12; and the notch 105 will be positioned so as to support from below the haptic 30 that is situated on the axial rearward side of the intraocular lens 14 accommodated in the stage 24, discussed later. The catch part 112 and the catch hole 118 may also be formed on the bottom face or side face of the insertion tool 10, for example.

In the intraocular lens insertion tool 10 having the above construction, first, the distal end section of the plunger 16 will be inserted from the rear into the main tubular section 18 of the tool body 12, and the hook part 116 positioned at an initial position engaged in the catch hole 11 8. Concomitantly, the support member 62 will be attached to the tool body 12 from below the base plate 31 in the manner described earlier. By so doing, the first support part 68 and the second support part 72 of the support member 62 will be held projected up above the resting face 32.

Figure 12:
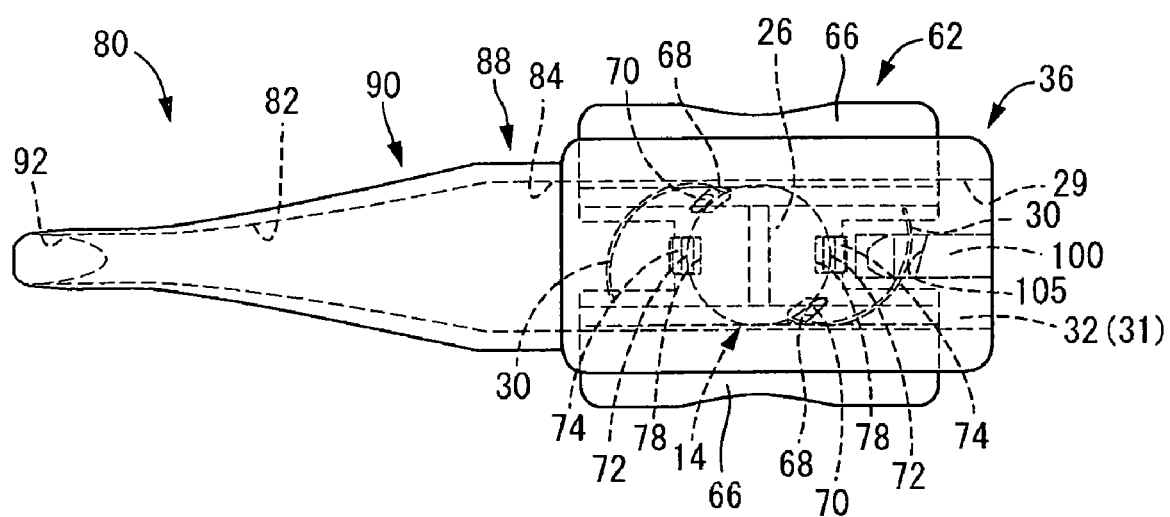
FIG. 12 is an enlarged top plane view of a principle part of the intraocular lens insertion tool of FIG. 1.
Figure 13:
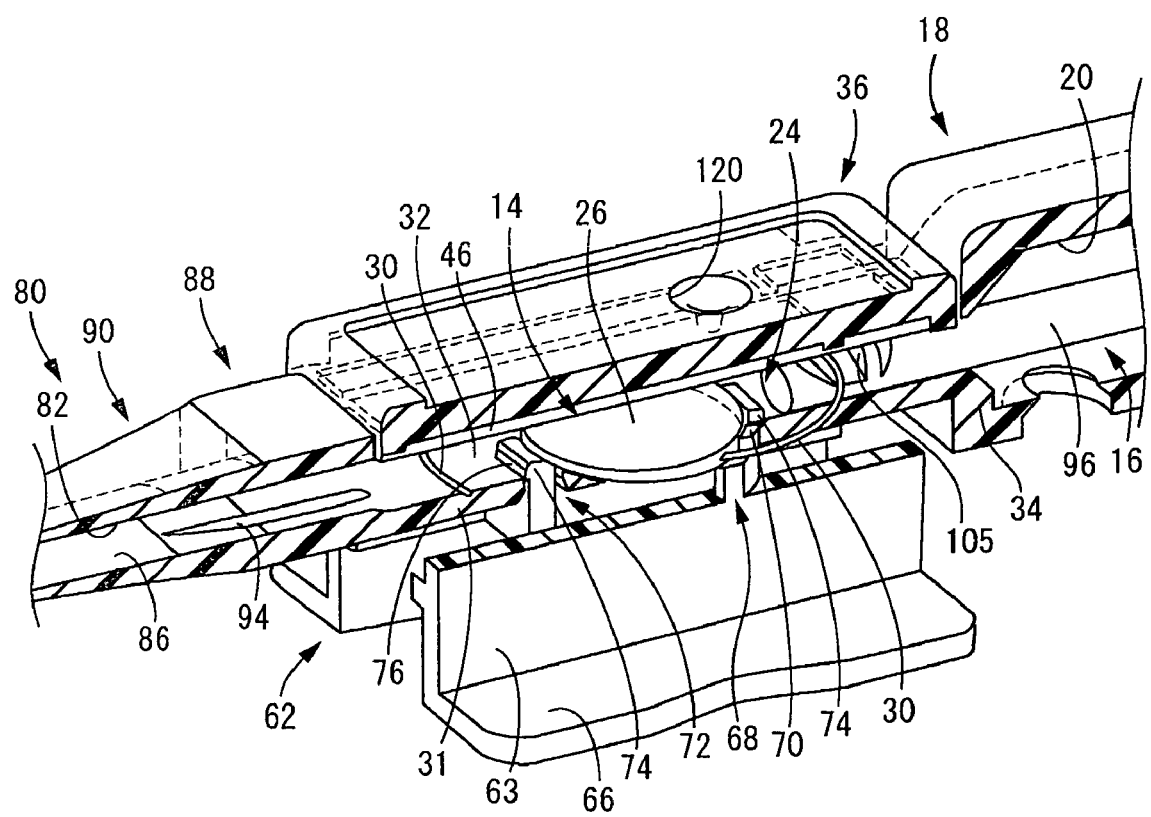
FIG. 13 is a partially cross sectional perspective view for explaining a way of operation of the intraocular lens insertion tool of FIG. 1.
Figure 14A:
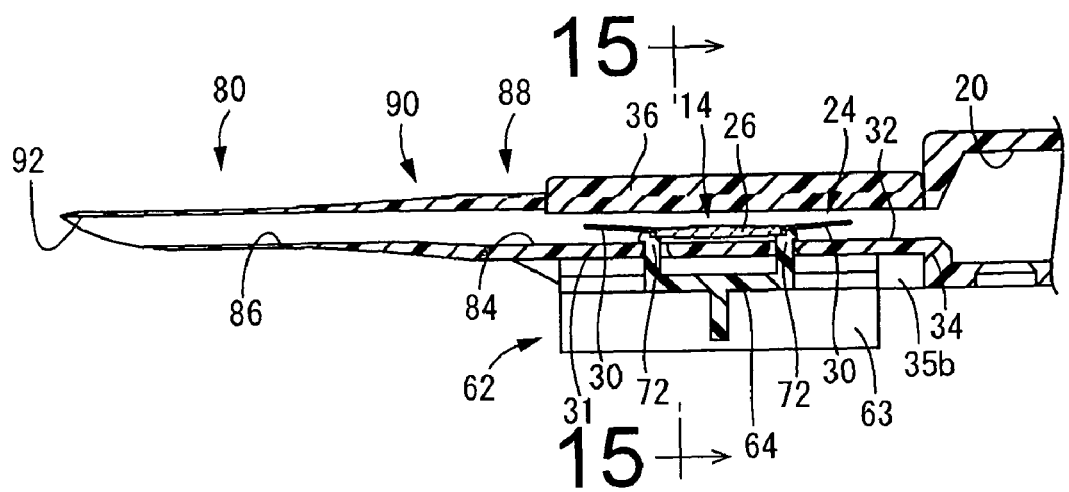
FIG. 14A is a view for explaining a supported state of the intraocular lens and FIG. 14B is a view for explaining a resting state of the intraocular lens rested on the resting face.

Then, as depicted in FIGS. 12 and 13, the outside peripheral section of the main body 26 of the intraocular lens 14 will be positioned resting on the upper end faces of the first support parts 68 and the second support parts 72. In FIG. 12, for ease of understanding, only the relevant section of the tool body 12, the intraocular lens 14, the support member 62, and the distal end section of the plunger 16 facing into the stage 24, are shown. As depicted in FIG. 14A, in this resting state the intraocular lens 14 will be supported with the outside peripheral section of its main body 26 in a state of contact with the first and second support parts 68, 72, while its center section is supported in a noncontact state with a prescribed gap between it and the resting face 32 in the vertical direction. Thus, the support portions in the present embodiment include the first and second support parts 68, 72.

Also, in this resting state, the haptic 30 of intraocular lens 14 that is the one situated toward the axial back side of the tool body 12 will be supported by the base face of the notch 105 of the plunger 16. Further, with the plunger 16 in the initial position, the second support part 72 that projects from the resting face 32 will be positioned to the axial front side of the plunger 16 (the left side in FIG. 12). Thus, the second support part 72 that is positioned on the plunger 16 side (the right side in FIG. 12) will constitute a stopper for inhibiting forward progress of the plunger 16, making forward progress of the plunger 16 impossible until the second support parts 72 are retracted from above the resting face 32, as will be described later.

Additionally, the peripheral walls 70, 74 formed on the first support parts 68 and the second support parts 72 will be positioned to the diametrical outer side of the main body 26 of the intraocular lens 14; in the present embodiment in particular, the peripheral walls 70 that have been formed on the first support parts 68 will be positioned to either side of the intraocular lens 14 on a diagonal axis with respect to the axial direction of the tool body 12, while the peripheral walls 74 that have been formed on the second support parts 72 will be positioned to either side of the intraocular lens 14 in the axial direction of the tool body 12. The level of displacement of the intraocular lens 14 in the axial direction and the axis-perpendicular direction relative to the tool body 12 will be restricted thereby, and the intraocular lens 14 can be held in stable fashion.

The intraocular lens 14 will then be positioned accommodated within the tool body 12 by bending the bending part 40 so that the opening 29 of the stage 24 is covered by the cover part 36. The cover part 36 is maintained in the closed state through engagement of the catch piece 56 in the catch notch 60.

The intraocular lens 14 is accommodated in the insertion tool 10 is the above manner. The insertion tool 10 according to this embodiment, with the intraocular lens 14 accommodated therein, will then be subjected to a sterilization process etc., then packaged and shipped.

Figure 14B:
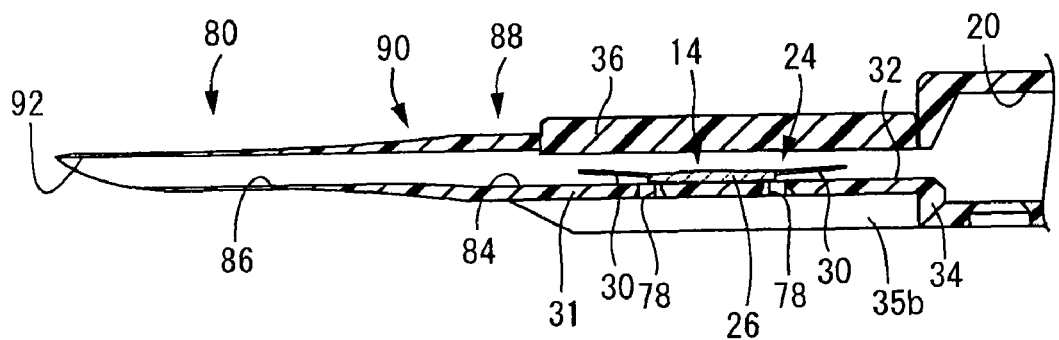

When the intraocular lens 14 is to be inserted into the eye using the insertion tool 10 according to the present embodiment, first, the support member 62 is pulled downward from the base plate 31 to detach it from the tool body 12. By so doing, as depicted in FIG. 14B, the first and second support parts 68, 72 which were supporting the intraocular lens 14 will be withdrawn downwardly from the resting face 32 and retract below the resting face 32. As a result, the intraocular lens 14 will be released from support by the first and second support parts 68, 72, so that the intraocular lens 14 now rests on the resting face 32. Here, because the resting face 32 in the present embodiment is defined by a flat face, the intraocular lens 14 can be positioned resting stably thereon; and because the width dimension of the resting face 32 is slightly larger than the diameter dimension of the main body 26 of the intraocular lens 14, rotation of the intraocular lens 14 in the circumferential direction on the resting face 32 will be prevented as well.

Then, with the distal end section of the nozzle part 80 inserted through a surgical incision made in the ocular tissue, the pusher plate 111 of the plunger 16 is pushed towards the tool body 12 side. By so doing, the tip of the plunger 16 will come into contact against the outside peripheral edge of the main body 26 of the intraocular lens 14 which is resting on the resting face 32, and the intraocular lens 14 will be guided towards the basal end orifice 84 by the plunger 16. Here, the amount of displacement in the left-right direction will be limited due to the fact that the rod-like part 100 of the plunger 16 is positioned between the guide projections 48, 48 that have been formed on the cover part 36, and the amount of displacement in the vertical direction will be limited by the center guide plate part 46. It will thus be possible for the plunger 16 to be plunged stably in the axial direction. Additionally, because the center guide plate part 46 and the left/right guide plate parts 44a, 44b project out towards the resting face 32, the amount of upward displacement of the intraocular lens 14 will be limited as well, thus making it possible for the intraocular lens 14 to be guided smoothly to the basal end orifice 84.

In preferred practice, prior to pushing the intraocular lens 14, an appropriate lubricant will be injected into the stage 24 or the nozzle part 80 if needed. In the present embodiment in particular, an injection hole 120 is formed passing through the cover part 36 in the thickness direction so that lubricant can be injected through the injection hole 120 with the cover part 36 closed; however, injection of lubricant could also be accomplished, for example, by injection through the distal end opening 92 of the nozzle part 80; by opening the cover part 36 and injecting lubricant from the opening 29 of the stage 24; or by withdrawing the plunger 16 from the tool body 12 and injecting lubricant from the orifice at the back end of the through-bore 20.

Then, the intraocular lens 14 which has been guided into the guide part 88 from the basal end orifice 84 by the plunger 16 will be guided into the constricted-diameter part 90 while being imparted with initial deformation to bowed shape with the center section of the main body 26 jutting downward by the guide projecting parts 94 that have been formed on the base face 86 of the guide part 88.

Next, by pushing in the plunger 16 further, the intraocular lens 14 will be guided towards the distal end direction inside the constricted-diameter part 90 while undergoing bowing deformation to even smaller size, after which it will be pushed to the outside of the insertion tool 10 from the distal end opening 92 of the nozzle part 80 and inserted into the eye. The maximum stroke length of the plunger 16 into the tool body 12 is limited through engagement of the distal end face of the pass-through part 98 by the wall part 34 of the through-bore 20, and at this maximum stroke length location, the distal end part of the plunger 16 will jut out slightly from the distal end opening 92. In this way, the intraocular lens 14 insertion operation is brought to completion.

In the insertion tool 10 constructed in this way, it will be possible to view the intraocular lens 14 housed inside the stage 24 through the cover part 36 from above the tool body 12. Additionally, the peripheral wall of the stage 24 (particularly the base plate 31) has unchanging thickness and sufficient thinness substantially throughout. Thus, with regard to the base plate 31, transmissivity of visible light will be high, and refraction and scattering will be kept to the minimum possible. As a result, the intraocular lens 14 housed inside the stage 24 will be clearly visible through the base plate 31 that constitutes the resting face 32. In the present embodiment in particular, in addition to the outside contours of the intraocular lens 14, the haptics 30 will be visible as well, so that the condition and position of the haptics 30 can be ascertained visually. Accordingly, in addition to discerning the presence/absence and position of the intraocular lens 14, it will also be possible to make an accurate visual assessment of the direction of the haptics 30 (in other words, the circumferential position of the intraocular lens 14); the condition of the haptics 30; the status of placement of the haptic 30 in the notch 105 of the plunger 16, and so on. In this way, according to the present embodiment it will be possible to view the intraocular lens 14 inside the stage 24 from either above or below so that the intraocular lens 14 insertion process can be carried out more easily. In the present embodiment in particular, the guide projecting parts 94 have been formed at locations away from the resting face 32, and the zone of the base plate 31 inclusive of the resting face 32 has flat surfaces on both front and back faces. Visibility may be further improved thereby.

Additionally, while the base plate 31 is thin, the side plates 35a, 35b connected to both widthwise edges of the base plate 31 have been formed with appreciable thickness, giving the stage 24 a generally "H" shaped axis-perpendicular cross section. Consequently, large cross sectional area will be ensured at the two widthwise edges of the base plate 31, and in the event that the base plate 31 is subjected to various kinds of external force or moment, it will be possible through the side plates 35a, 35b to establish large cross-sectional secondary moment, making it possible to efficiently ensure a high level of bending rigidity despite the thinness of the base plate 31. In the present embodiment in particular, because the side plates 35a, 35b are continuous with the walls at either widthwise side of the main tubular section 18 and have been formed extending across the entirety of the tool body 12 with the exception of a nozzle part 80, it will be possible to ensure greater rigidity. Furthermore, because the axial back edge part of the base plate 31 is given appreciable thickness by being connected with the wall part 34, further improvements in rigidity may be afforded by the wall part 34. In addition, by closing the cover part 36, further enhanced reinforcing action can be provided. Also, because the base plate 31, the side plates 35a, 35b, the wall part 34, and the cover part 36 are constituted by an integrally formed component, it will be possible through a simple structure to ensure sufficient strength of the base plate 31, as well as to simplify manufacture.

Additionally, with the support member 62 attached to the base plate 31, the mating projection 79 will slip between the side plates 35a, 35b of the tool body 12 and be positioned in contact with or proximity to the side plates 35a, 35b. Thus, when the side plates 35a, 35b experience deformation due to external forces or the like, any further deformation thereof will be inhibited through contact against the mating projection 79 so at to provide reinforcing action. Also, the mating structure of the mating projection 79 and the side plates 35a, 35b constitutes a guide mechanism during attachment or detachment of the support member 62 to and from the tool body 12, making it possible for the operation to attach or detach the support member 62 to and from the tool body 12 to be carried out more easily.

In the present embodiment in particular, because the support member 62 has leg plate parts 66 that spread outwardly, the strength of the support member 62, and hence the strength of the tool body 12 (which is reinforced by the support member 62), can be further improved. Additionally, since the leg plate parts 66 can be grasped during attachment or detachment of the support member 62 to and from the tool body 12, ease of operation during attachment or detachment can be improved as well.

Furthermore, with the intraocular lens 14 supported by the first and second support parts 68, 72, only the outside peripheral section of the main body 26 of the intraocular lens 14 is supported by the first and second support parts 68, 72 while being supported above and separated from the resting face 32 in a noncontact state. With this arrangement, a risk that the center section of the main body 26 will be damaged can be reduced. The peripheral walls 70, 74 provided to the first and second support parts 68, 72 will restrict the level of displacement of the intraocular lens 14, whereby even in the case where the intraocular lens insertion tool 10 will be shipped with the intraocular lens 14 accommodated therein and be subjected to vibration during transportation or inclination during surgery, problems such that the intraocular lens 14 will be appreciably displaced within the intraocular lens insertion tool 10 and bump against the resting face 32 or the cover part 36 are avoided. Therefore, a risk that the intraocular lens 14 will be damaged during the bump can be reduced while even in the case where the intraocular lens insertion tool 10 will be subjected to such vibration, it is possible to advantageously keep the intraocular lens 14 from shifting out of position and to rest the intraocular lens 14 above the resting face 32 with excellent precision of positioning.

Additionally, in the present embodiment, the catch hooks 76 that hold the support member 62 in a state of attachment to the tool body 12 and that hold the first and second support parts 68, 72 in a state of projection above the resting face 32 have been integrally formed with the second support part 72. It will therefore be possible for the second support parts 72 to be disposed in direct engagement with the resting face 32 and for the first and second support parts 68, 72 to project precisely from prescribed locations on the resting face 32. The catch mechanism for attaching the support member 62 to the tool body 12 can be produced with excellent space efficiency, and a restraining sensation can be imparted when the catch hooks 76 have been successfully projected up from the resting face 32, so that it can be ascertained that the support member 62 has been attached correctly.

When using the insertion tool 10 of the present embodiment, it is possible for the intraocular lens 14 to be rested on the resting face 32 by a very simple operation, namely, of detaching the support member 62 from the tool body 12. In the insertion tool 10 of the present embodiment, consistent precision of positioning is afforded by the first and second support parts 68, 72 as mentioned previously, while the state of the intraocular lens 14 is viewable from the outside through the cover part 36 or the base plate 31. Therefore, despite the simplicity of the operation, it will be possible for the intraocular lens 14 to be rested on the resting face 32 with excellent positioning accuracy. In this embodiment in particular, every through-hole 78 through which the first and second support parts 68, 72 are inserted is formed on the resting face 32, whereby it is possible to directly view the intraocular lens 14 through the through-holes 78 after detaching the support member 62 from the base plate 31. Accordingly, it is possible to discern the presence/absence and condition of the intraocular lens 14 more reliably and easily.

Further, because the intraocular lens 14 is rested with the opening 29 of the stage 24 maintained covered by the cover part 36, the intraocular lens 14 can be prevented from falling out from the insertion tool 10. A hygienic advantage is provided as well, due to reduced likelihood of contact of the intraocular lens 14 with the outside environment.

Figure 16:
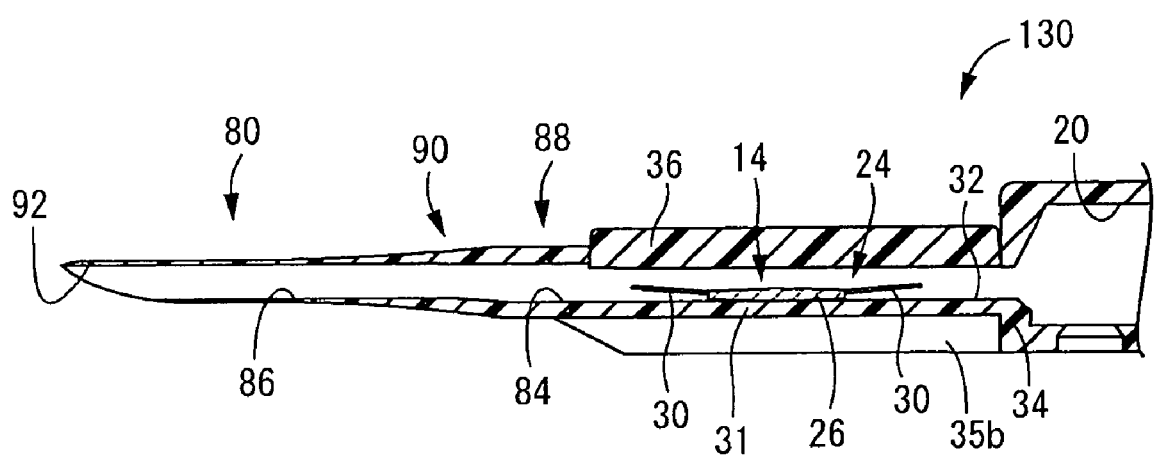
FIG. 16 is a top plane view of an intraocular lens insertion tool according to a second embodiment of the present invention.

Next, FIG. 16 depicts an intraocular lens insertion tool 130 according to a second embodiment of the present invention. In the following description, elements like those in the first embodiment described above shall be designated by like reference numerals and will not be discussed in detail. The intraocular lens insertion tool 130 according to the second embodiment has a generally identical construction with that of the intraocular lens insertion tool 10 of the first embodiment, and accordingly only a part which corresponds to FIG. 14A of the first embodiment is shown.

The support member 62 of the above-described first embodiment is absent from the intraocular lens insertion tool 130 according to the present embodiment. Specifically, the base plate 31 of the insertion tool 130 has a planar surface which has no perforating through-holes 78 of the first embodiment. The intraocular lens insertion tool 130 according to the present embodiment will be provided in addition to the intraocular lens 14. Prior to surgery, the cover part 36 is opened and the separately provided intraocular lens 14 is rested on the resting face 32. Then the cover part 36 is closed, thereby housing the intraocular lens 14 inside the stage 24. In the same way as the first embodiment, the plunger 16 is plunged so that the intraocular lens 14 will be inserted into the eye.

While the invention has been described detail herein in terms of certain preferred embodiments, these embodiments are merely exemplary, and the specific disclosure herein should not be construed as limiting in any way.

For example, the cover part 36 may be constituted as a separate member from the tool body 12. Moreover, it would be acceptable to provide the insertion tool 10 with the intraocular lens 14 housed within the stage 24 while fastening the cover part 36 to the tool body 12 so as to render the cover part 36 unable to be opened. With this arrangement, it would be possible to keep the intraocular lens 14 from being contaminated or being dropped off the stage 24 due to unnecessary opening operation of the cover part 36, whereby safety and reliability can be improved.

It is not essential for the catch mechanism (locking mechanism) that fastens the support member 62 to the tool body 12 to be formed on the second support parts 72, as were the catch hooks 76 formed on the second support parts 72 described earlier. In place of the catch hooks 76, it would be possible for example to give the first support parts 68 and the second support parts 72 contours with gradually increasing dimension in top view towards the leg plate part 66 side, and by forcing these first support parts 68 and the second support parts 72 into the through-holes 78 formed the resting face 32, to fasten the support member 62 to the lower side of base plate 31 through the recovery force of the through-holes 78 and frictional force between the members; or to fasten the side wall parts 63, 63 of the support member 62 by clasping them between the side plates 35a, 35b.

Furthermore, while the intraocular lens 14 accommodated in the insertion tool 10, 130 has a main body 26 and haptics 30 that are formed as separate elements, it would of course be possible for the main body 26 and the haptics 30 to be integrally formed by the same component.

What is claimed is:

1. An intraocular lens insertion tool comprising:
    a tool body of generally tubular shape for accommodating an intraocular lens positioned therein, and including an insertion tube section disposed at an distal end section of the tool body in an axial direction; and
    a plunging member adapted to be inserted into the tool body from a rear in the axial direction and adapted to be moved forward for inserting into an eye the intraocular lens, wherein
    a resting portion that communicates with a basal end part of the insertion tube section is integrally formed with the tool body,
    the resting portion includes a resting face in a form of a flat-shaped base plate adapted for resting thereon the intraocular lens which is ready for inserting into the eye, and a pair of side plates that project in an up and down direction relative to the base plate thereby imparting to the resting portion a generally "H" shaped cross section,
    the side plates have a thickness dimension greater than a thickness dimension of the base plate, and
    the tool body inclusive of the resting portion and the insertion tube section is integrally formed from light-transmissive synthetic resin material whereby the intraocular lens positioned resting on the resting face of the resting portion is viewable from an outside through the base plate.

2. The intraocular lens insertion tool according to claim 1, wherein through-holes are formed in the base plate; a support member is adapted to be attached to the base plate from the outside, and support portions that project out from the support member are adapted to be passed through the through-holes so as to project out on the resting face for supporting an outside peripheral section of the intraocular lens in the resting portion with a prescribed gap between the resting face and a center section of the intraocular lens; and support of the intraocular lens by the support portions is adapted to be released by downwardly displacing the support member with respect to the base plate to extract the support portions which projected out on the resting face and position the intraocular lens resting on the resting face.

3. The intraocular lens insertion tool according to claim 1, wherein the resting portion is provided with an opening that opens to an outside of the tool body, and with a cover body adapted to cover the opening.

4. The intraocular lens insertion tool according to claim 1, wherein the support member is provided with a mating projection adapted to slip between opposing faces of the pair of side plates that have been formed at two widthwise edges of the base plate; and the mating projection is provided with leg plate parts extending beyond the side plates and flaring to either side in a width direction of the base plate.

5. The intraocular lens insertion tool according to claim 1, wherein the base plate of the resting portion has a thickness dimension of 3 mm or less.

6. The intraocular lens insertion tool according to claim 1, wherein a thick wall part is provided at an axial back edge part of the base plate in an axial direction of the tool body.

* * * * *